US006686428B2

(12) United States Patent
Zhang et al.

(10) Patent No.: US 6,686,428 B2
(45) Date of Patent: Feb. 3, 2004

(54) METAL CATALYZED REACTIONS

(75) Inventors: Xumu Zhang, University Park, PA (US); Aiwen Lei, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 10/108,420

(22) Filed: Mar. 29, 2002

(65) Prior Publication Data

US 2002/0193543 A1 Dec. 19, 2002

Related U.S. Application Data

(60) Provisional application No. 60/280,275, filed on Mar. 30, 2001.

(51) Int. Cl.⁷ .............................................. C08F 38/02
(52) U.S. Cl. ..................... 526/285; 526/134; 526/110; 526/115; 526/117; 568/6
(58) Field of Search ................................ 526/134, 285

(56) References Cited

FOREIGN PATENT DOCUMENTS

WO    WO 95/20569 A1  *  8/1995  .........  C07C/249/12

OTHER PUBLICATIONS

Zhou, S.–M.; Yan, Y.–L.; Deng, M.–Z. Synlett 1998, 2, 198.*
Rossi, R.; Bellina, F.; Carpita, A. Synlett 1996, 4, 356.*
Sai, H.; Ogiku, T.; Nishitani, T.; Hiramatsu, H.; Horikawa, H.; Iwasaki, T. Synthesis 1995, 5, 582.*
Sato, M.; Miyaura, N.; Suzuki, A. Chemistry Letts. 1989, 8, 1405.*
Tanaka, K.; Katsumura, S. Organic Letts. 2000, 2, 373.*
Goossen, L. J. Chem. Commun. 2001, 7, 669.*
Kosugi, M.; Koshiba, M.; Sano, H.; Migita, T. Bull. Chem. Soc. Jpn. 1985, 58, 1075.*
Stefani, H. A.; Costa, I. M.; Zeni, G. Tetrahedron Letts. 1999, 40, 9215.*

* cited by examiner

*Primary Examiner*—David W. Wu
*Assistant Examiner*—Rip A Lee
(74) *Attorney, Agent, or Firm*—McDermott, Will & Emery

(57) ABSTRACT

Compositions and processes of forming chemical bonds, such as carbon-carbon and carbon-heteroatom bonds are provided. The compositions include at least one α-halo carbonyl compound, and one or more transmetallation reagents. The transmetallation reagents are formed by the addition of a metal or metal catalyst to a target compound. The target compound is the compound undergoing chemical bond formation. Bond formation can be carried out in both intermolecular reactions (i.e. between two or more target compounds), or intramolecular (within the same target compound) reactions.

19 Claims, No Drawings

METAL CATALYZED REACTIONS

CROSS-REFERENCE TO RELATED APPLICATION

This application claims priority from U.S. provisional patent application Ser. No. 60/280,275 filed Mar. 30, 2001 entitled Transition Metal Catalyzed Reactions, the entire disclosure of which is incorporated herein by reference.

The subject matter of this application was made with support of the National Institutes of Health under Grant No. 1R01 GM 58832. The Government has certain rights in the invention.

FIELD OF THE INVENTION

The present invention relates to a composition and process of forming chemical bonds, such as carbon-carbon and carbon-heteroatom bonds. The present invention has particular applicability to the formation of chemical bonds by transmetallation reaction chemistry.

BACKGROUND

Over the past several decades, palladium (Pd) catalyzed carbon-carbon bond formation reactions have been extensively studied and widely applied in organic synthesis [Tsuji, J. *Transition Metal Reagents and Catalysis,* John Wiley: Chichester, 2000]. The ultimately formed chemical bonds are produced by a sequence of intermediates. These include the formation of an aryl or alkenylpalladium halide complex generated by oxidative addition of the aryl or alkenylhalide with Pd. These complexes can, in turn, undergo transmetallation with many reagents. This reaction sequence is followed by reductive elimination to form a carbon-carbon bond and to regenerate a Pd (0) species. This system provide a methods for developing many crosscoupling reactions. The following authors are known to employ the element in the parentheticals for coupling reactions: Suzuki (boron, B), Stille (tin, Sn), Negeshi (zinc and aluminum, Zn and Al), Kumada (magnesium, Mg) [Miyaura, N.; Suzuki. A. *Chem. Rev.* 1995, 95, 2457; Knight, D. W. In *Comprehensive Organic Synthesis;* Trost, B. M.; Fleming, I., Ed.; Pergamon Press: Oxford, 1991, Vol 3, Chapter 2.3; Suzuki, A. *Pure Appl. Chem.* 1985, 57, 1749; Tamao, K.; Kumada, M. in *The Chemistry of the Metal-Carbon Bond* (Ed., F. R. Hartley), Vol. 4, Wiley, N.Y., 1987, Chapter 9 p 819; Suzuki, A. *Pure Appl. Chem.* 1985, 57, 1749; Stille, J. K. Angew Chem. Int. Ed. Engl. 1986, 25, 508; Negishi, E. *Acc. Chem. Res.* 1982, 15, 340. (i) Kumada, M. *Pure Appl. Chem.* 1980, 52, 669].

In contrast, palladium-catalyzed homocoupling reactions have not been studied extensively, although some homocoupling reactions of aryl and alkenyl halides facilitated by a Pd species are known. [See, e.g., Hennings, D. D.; Iwama, T.; Rawal, V. H. *Org. Lett.* 1999, 1, 1205; Hassan, J.; Penalva, V.; Lavenot, L.; Gozzi, C.; Lemaire, M. *Tetrahedron* 1998, 54, 13793; Jutand, A.; Mosleh, A. *J. Org. Chem.* 1997, 62, 261; Smith, K. A.; Campi, E. M.; Jackson, W. R.; Marcuccio, S.; Naeslund, C. G. M.; Deacon, G. B. *Synlett,* 1997, 131; Jutand, A.; Mosleh, A. *Synlett,* 1993, 568; Jutand, A.; Negri, S.; Mosleh, A. *Chem. Commun.,* 1992, 1792; Miura, M.; Hashimnoto, H.; Itoh, K.; Nomura, M. *Chem. Lett.* 1990, 459]. Other known coupling reactions include Glazer coupling (Chem Ber 1869, 2, 422, Cadiot P, Chodkiewwicz, W. Chemistry of Acetylenes, 1969, Marcel Dekker, New York, p 597), Ullman-type Coupling reactions (Semmelhack, M. F.; Helwuist, P. M.; Jones, L. D. J. Am. Chem. Soc. 1971, 93 5908; Kende, A.; Liebeskind, L. S. Braitsch, D. M. Tetrahedron Lett. 1975, 3375; Prerce, V.; Bae, J. Y.; Zhao, M.; Hill, D. H. J. Org. Chem. 1994, 60, 176). For forming carbon-heteroatom bonds, Hartwig and Buchwald have made a couple of catalysts. Hartwig, J. F. Angew Chem. Int. Ed. Engl. 1998, 37, 2047; Wolfe, J. P.; Wagaw, S.; Buchwald, S. L. J. Am. Chem. Soc. 1996, 118, 1133; Mann, G.; Hartwig, J. F. J. Org. Chem. 1997, 62, 5413).

The following table summarizes coupling reactions.

Metal-Mediated Coupling Reactions

Glaser Coupling

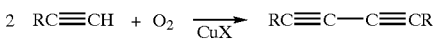

Kumada Coupling

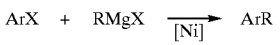

Ullman Coupling

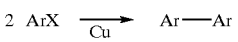

Negishi Coupling

Sonogashira Coupling

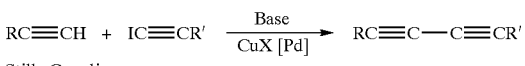

Stille Coupling

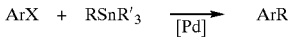

Hartwig-Buchwald Coupling

Suzuki Coupling

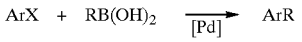

X = I, Br, Cl, OTf; CuBr, CuCl, [Pd] = Pd(PPh3)4, PdCl2(PPh3)2, PdCl2(dppf), Pd2(dba)3 + bisphosphine, Pd(OAc) + bisphosphine

[Ni] = NiCl2(PPh3)2, NiCl2(dppp), NiCl2 + DIBAH, NiCl2(dppf)

Base = NaHCO3, NaOR, Et3N, Et2NH, KF, Na2CO3, KOH

Although the above mentioned metal-catalyzed and metal-facilitated carbon-carbon and carbon-heteroatom bond formation reactions are useful for organic synthesis, they are also limited. For example, an Ullman coupling reaction generally is carried out under harsh conditions and many hindered or aryl halides having one or more electron donating groups resist coupling. Glaser coupling requires the presence of oxygen, which can destroy many sensitive products, particularly diynes. A number of alkynes with functional groups do not undergo coupling in a Glaser coupling reaction. Moreover, the coupling reaction is generally not applicable to polymerization or oligomerization reactions.

The synthesis of diynes is particularly problematic as diynes are not stable and prone to decomposition. Therefore, only alkyl halides, aryl halides (e.g., RI or RBr) that react under mild conditions will couple. In Sonogashira, Suzuki, Stille, Negishi, Kumada, Hartwig-Buchwald coupling reactions, oxidative addition of aryl halides can be a difficult step. This is particularly true if the aryl halide has two groups substituted in adjacent positions. To minimize or avoid the oxidative addition of these difficult substrates would be of great interest in organic synthesis. For a Suzuki coupling reaction, a known side reaction product is dehalogenation reaction. In Sonogashira, Suzuki, Stille, Negishi, Kumada, Hartwig-Buchwald coupling reactions, the oxidative addition of RX when R is a simple alkyl group with a β-hydrogen is a slow process and metal compounds can easily form undesirable β-hydrogen elimination products. This has been a major limitation of these coupling reactions.

Hence, there is a need for metal-catalyzed catalytic reactions which can improve coupling reactions, or, ideally, overcome many of the limitation of prior art processes. There is also a need in the chemical industry for making existing pharmaceutical products, agrochemical products, polymers products and as well as new products by a facile chemical bond forming reaction.

SUMMARY OF THE INVENTION

An advantage of the present invention is a composition for chemical bond formation.

An additional advantage of the present invention is a method of forming chemical bonds by transmetallation.

Additional advantages, and other features of the present invention will be set forth in the description which follows and in part will become apparent to those having ordinary skill in the art upon examination of the following or may be learned from the practice of the present disclosure. The advantages may be realized and obtained as particularly pointed out in the appended claims.

According to the present invention, the foregoing and other advantages are achieved in part by a composition comprising at least one α-halo carbonyl compound; and one or more transmetallation reagents.

Embodiments include, compositions having a base, e.g. a compound having an available pair of electrons. The forgoing bases include triethyl amine ($Et_3N$), DABCO, $Et_2NH$, $NaOR^b$, $Na_2CO_3$, KF, $K_3PO_4$, NaOAc, KOH, and $R^bNX$, where $R^b$ is one or more of an H, alkyl groups and X is an anion, such as a halogen or ester. The composition includes at least one transmetallation reagent. This reagent can be prepare prior to forming the composition or in situ.

Transmetallation reagents are formed by the addition of a metal or metal catalyst to a target compound. The target compound is the compound undergoing chemical bond formation. For example, transmetallation reagents include metal complexes, such as RM, $RB(OH)_2$, $RBR'_2$, $RSnR'_3$, RZnX, RHgX, RMgR, $RSiR'_3$, RCu, ROM, RNHM, RAlR'2, wherein R and R' are independently an aryl or alkyl group and M is a metal. Other organometallic species are also contemplated. Additionally, an α-halo carbonyl species which can easily undergo oxidative addition with redox active metals is included in this composition for coupling reactions.

Another aspect of the present invention is forming chemical bonds. Bond formation can advantageously be carried out in both intermolecular reactions (i.e. between two or more target compounds), or intramolecular (within the same target compound) reactions. Chemical bond formation methods can be used to make biologically active compounds or polymers, such as SP-carbon type of molecules. The method comprises combining at least one transmetallation reagent comprising a target compound with at least one α-halo carbonyl compound; and forming a bond to or within the target compound of the transmetallation reagent.

In another aspect of the invention, a process for hydroboration and asymmetric hydroboration of boric compounds and coupling of bisboronic compounds by either intramolecular or intermolecular coupling is contemplated. The process comprises: combining at least one α-halo carbonyl compound with at least one transmetallation reagent comprising a boric compound; and coupling the boric compound.

Additional advantages of the present invention will become readily apparent to those skilled in this art from the following detailed description, wherein only the preferred embodiments of the present invention are shown and described, simply by way of illustration but not limitation. As will be realized, the invention is capable of other and different embodiments, and its several details are capable of modification in various obvious respects, all without departing from the spirit of the present invention. Accordingly, the drawings and description are to be regarded as illustrative in nature, and not as restrictive.

DETAILED DESCRIPTION OF THE INVENTION

The present invention relates to a composition and process of forming chemical bonds, such as carbon-carbon and carbon-heteroatom bonds. The present invention has particular applicability to the formation of chemical bonds by transmetallation reaction chemistry.

In an embodiment of practicing the present invention, at least one α-halo carbonyl compound, e.g. an α-bromo carbonyl compound, is combined with at least one transmetallation reagent comprising a target compound; and forming a chemical bond to or within the target compound. Bond formation can advantageously be carried out in both intermolecular reactions (i.e. between two or more target compounds, such as in coupling reactions), or intramolecular (i.e. within the same target compound, such as an oxidation reaction) reactions.

In one aspect of the practicing the method a base is also combined with the transmetallation reagent and α-halo carbonyl compound. Useful bases in transmetallation chemistry are known and include triethyl amine ($Et_3N$), DABCO, $Et_2NH$, $NaOR^b$, $Na_2CO_3$, KF, $K_3PO_4$, NaOAc, KOH, and $R^bNX$, where $R^b$ is one or more of an H, alkyl groups and X is an anion, such as a halogen or ester.

It is contemplated that the transmetallation reagent can be prepare prior to the intended bond forming reaction or in situ. The transmetallation reagents can be formed by the addition of a metal or metal catalyst to a target compound. The target compound is the compound undergoing chemical bond formation. The transmetallation reagent can include one or more elements consisting of B, Sn, Al, Zn, Mg, Zr, Cu, Hg, and Si or organometalic species. For example, transmetallation reagents include metal complexes, such as RM, $RB(OH)_2$, $RBR'_2$, $RSnR'_3$, RZnX, RHgX, RMgR, $RSiR'_3$, RCu, ROM, RNHM, RAlR'2, where R and R' are the target compounds and wherein R and R' are independently an aryl or alkyl group and M is a metal. Other organometallic species are also contemplated. Additionally, an α-halo carbonyl species which can easily undergo oxidative addition with redox active metals is included in this composition for coupling reactions.

The transmetallation reagents can be formed by adding a target compound to a catalyst or catalyst complex. These are known in the art and include transition metal catalysts, such as Pd(0), Ni(0), Rh(I), Pt(0), Ir(0), Cu(I), Mo(0), Mo(II), and Ru(II) catalysts with or without ligands as known in the art.

The catalyst can be selected from the group consisting of $PtCl_2$; $H_2PtCl_4$; $Pd_2(DBA)_3$; $Pd(OAc)_2$; $PdCl_2(RCN)_2$; $PdCl_2$(diphosphine); $[Pd(allyl)Cl]_2$; $Pd(PR_3)_4$; $[Rh(NBD)_2]X$; [Rh (NBD)$Cl]_2$; $[Rh(COD)Cl]_2$; $[Rh(COD)_2]X$; $Rh(acac)(CO)_2$; $Rh(ethylene)_2(acac)$; $[Rh(ethylene)_2Cl]_2$; $RhCl(PPh_3)_3$; $Rh(CO)_2Cl_2$; $RuHX(L)_2$; $RuX_2(L)_2$; Ru(arene)$X_2$(diphosphine); Ru(aryl group)$X_2$; $Ru(RCOO)_2$(diphosphine); Ru(methallyl)2(diphosphine); Ru(aryl group)$X_2(PPh_3)_3$; Ru(COD)(COT); Ru(COD)(COT)X; $RuX_2$(cymen); $Ru(COD)_n$; Ru(aryl group)$X_2$(diphosphine); $RuCl_2$(COD); $(Ru(COD)_2)X$; $RuX_2$(diphosphine); $RuCl_2$(=CHR)($PR'_3)_2$; $Ru(ArH)Cl_2$; $Ru(COD)(methallyl)_2$; (Ir$(NBD)_2Cl)_2$; $(Ir(NBD)_2)X$; $(Ir(COD)_2Cl)_2$; $(Ir(COD)_2)X$; CuX $(NCCH_3)_4$; Cu(OTf); $Cu(OTf)_2$; Cu(Ar)X; CuX; $Ni(acac)_2$; $NiX_2$; $(Ni(allyl)X)_2$; $Ni(COD)_2$; $NiCl_2$(diphosphine); $MoO_2(acac)_2$; wherein each R and R' is independently selected from the group consisting of: alkyl or aryl; Ar is an aryl group; and X is a counteranion such as I, Br, Cl, OTf, $BF_4$, $SbF_6$, $BAr_4$; and L represents a ligand.

Diphosphine include dppe, dppp, dppb, dppf, rac-Binap, chiral bisphosphines, DuPhos, BINAP, BPPM, DIPAMP, DIOP, MCCPM, BCPM, BICP, PennPhos, BPE, ChiraPhos, NorPhos, Degphos, BPPFA, JosiPhos, TRAP, TolBINAP, H8-BINAP, BINAPO, MOP, BINAPHOS, BIPHEMP, SEGPHOS, TUNAPHOS, KetalPhos, f-KetalPhos, HydroPhos, f-HydroPhos, Binaphane, f-Binaphane, FAP; and the mono phosphine includes: $PPh_3$, $P(o-tolyl)_3$, tri(2,6-dimethylphenyl)phosphine, $P^tBu_3$, $PCy_3$, $P(2-Furyl)_3$ and $PPh_2(o-ArC_6H_4)$.

In practicing an embodiment of the invention a transmetallation reagent is combined with at least one α-halo carbonyl compound. Through a metal-enolate intermediate, the same or different transmetallation reagents can be transferred to a metal center and reductive elimination gives the desired product. These reactions can advantageously be carried out to form both intermolecular and/or intramolecular bonds. The method can be used to make biologically active compounds or polymers, such as SP-carbon type formation of molecules. An example of a metal mediated crosscoupling reaction is provided below.

Metal-Mediated Coupling Reactions

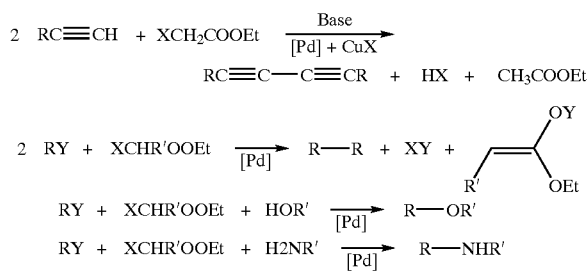

R = Alkyl, Aryl, Alkenyl, Y = ZnX, $B(OH)_2$ and other transmetallation reagents Double transmetallation through metal-enolates is also contemplated as an aspect of the present invention. In one aspect, the present invention relates to transition metal complexes with phosphine ligands as catalysts and an α-halocarbonyl compound as a reagent for oxidative addition. The transmetallation reagents can be (R—M) where R is an alkyl or aryl group, M contains B, Al, Sn, Zn, Mg, Si, Li, Cu, Hg, Zr, with or without other elements. Sometimes, substrates for the ligand exchanging reaction are ROH, $RNH_2$, RN(R')H, RSH, CN and $R_2P(O)H$. The transition metal complexes are useful as catalysts in homocoupling reaction, intramolecular cross-coupling reactions and other transformations.

Scheme 1 illustrates possible mechanisms of a Pd-catalyzed crosscoupling and homocoupling reactions. In the palladium-catalyzed crosscoupling reaction, the reaction is initiated by oxidative addition of $R^1$—X to Pd, followed by transmetallation of $R^2$—M, and reductive elimination of $R^1$ and $R^2$ gives the coupling product ($R^1$-$R^2$) (Scheme 1, path A). If the reductive elimination of $R^1$ and $R^2$ is slow, $Pd(R^2)_2$ can be generated and Pd—$R^1$ can be transmetallated again with another $R^2$—M (double transmetallation). Reductive elimination of $Pd(R^2)_2$ leads to a homocoupling product (Scheme 1, path B). It is believed that there is no report of the intermediate (I), derived from oxidative addition of $R^1$X to a Pd (0) species, undergoing double transmetallation with $R^2$—M to form an intermediate (III). Although not completely understood, the second transmetallation, i.e., replacing the $R^1$ group with $R^2$ in the intermediate II, may be an aspect in a palladium-catalyzed homocoupling reaction. In this example, the target compound $R^2$ undergoes chemical bond formation with itself by a homocoupling reaction.

Scheme 1

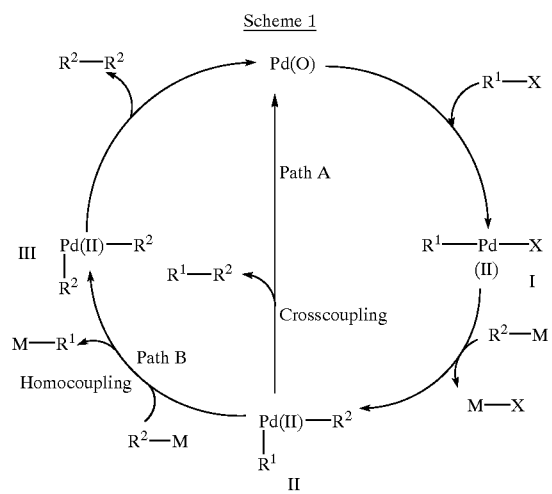

Recently, considerable attention has been devoted to the palladium enolate chemistry [Wang, Z.; Zhang, Z. Lu, X. *Organometallics* 2000, 19, 775; Kawatsura, M.; Hartwig, J. F. *J. Am. Chem. Soc.* 1999, 121, 1473; Åhman, J.; Wolfe, J. P.; Troutman, M. V.; Palucki, M.; Buchwald, S. L. *J. Am. Chem. Soc.* 1998, 120, 1918; Sodeoka, M.; Shibasaki, M. *Pure Appl. Chem.* 1998, 70, 411 ] Several palladium enolate complexes have been well-characterized.

It is believed that the first transmetallation of an organoboron reagent to a palladium enolate was not reported or recognized previously. Through investigation and experimentation, it was demonstrated that an enolate anion can serve as a leaving group similar to a bromide or iodide in a transmetallation process. Since oxidative addition of readily available a-bromocarbonyl compounds to a palladium (0) species can also readily occur, double transmetallation can be carried out. This double transmetallation reaction is depicted below. Here, an alpha-bromo phenyl carbonyl compound give a Pd(II)Br(enolate) intermediate (I), double transmetallation with aryl boronic acids yields an intermediate(III), which leads to a homocoupling product through reductive elimination.

Scheme 2

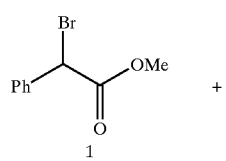

1

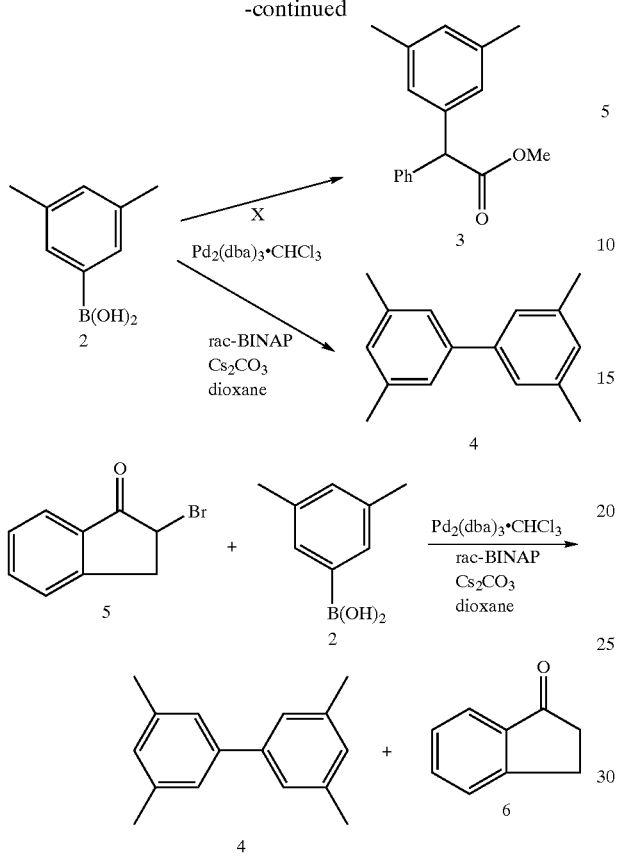

As an example of this type of intramolecular bond formation, methyl α-bromophenyl acetate ester 1 (1.0 mmol) and 3,5-dimethyl phenyl boronic acid 2 (1.2 mmol) were used as reagents for Pd-catalyzed homocoupling reactions. With these reagents, the homocoupling product 4 was obtained in 70% yield exclusively under conditions with $Pd_2(dba)_3 \cdot CHCl_3$ (0.025 mmol), rac-BINAP (0.05 mmol) and $Cs_2CO_3$ (1.5 mmol) in dioxane (5 mL). When KF was used to replace $Cs_2CO_3$, an improved yield of the homocoupling product (97%) was obtained. With an α-bromo ketone 5, 6 and a homocoupling product 4 were obtained (Scheme 2).

To explore the scope of this reaction, the examination of several aryl boronic substrates and other α-bromo carbonyl compounds were investigated (Table 1). Using ethyl α-bromo acetate ester 7, both homocoupling and crosscoupling products were observed (Table 1, entries 1, 3–5, 7, 9 and 12). Interestingly, substitution at the α-position of α-bromo carbonyl compounds (e.g., 1) promotes the homocoupling reaction and inhibits the crosscoupling reaction (Table 1, entries 3 and 5). Furthermore, addition of water influences the selectivity between homocoupling and crosscoupling products in this system. For example, in the presence of water, the ratio of homocoupling and crosscoupling product switched from 30:70 to 70:30 in the coupling reaction of ortho-methyl phenyl boronic acid and ethyl α-bromide acetate ester (Table 1, entries 3 and 4). When the reaction was carried out using an α-substituted bromocarbonyl compound in the presence of water, only homocoupling products were observed for many substrates, i.e., target compounds (Table 1, entries 2, 6, 8, and 10–17). It is noteworthy that this novel homocoupling coupling reaction appears to tolerate a variety of functional groups, e.g., aldehyde, methoxy, nitro groups, etc. The presence of an ortho-methoxyl group in aryl boronic acids also gave high yields of the homocoupling product (see, e.g., different selectivities in entries 3, 12 and 14).

TABLE 1

Palladium-catalyzed Coupling Reaction of Aryl Boronic Acids[a]

| | | | |
|---|---|---|---|
| | | | |

| | | | | products[b] | |
|---|---|---|---|---|---|
| entry | substrates | | solvent | yields (%) | Homo | Cross |
| 1 | 2a | 7 | dioxane | 89 | 50 | 50 |
| 2 | 2a | 1 | dioxane/$H_2O$ | 95 | 100 | 0 |
| 3 | 2b | 7 | dioxane | 82 | 30 | 70 |
| 4 | 2b | 7 | dioxane/$H_2O$ | 89 | 70 | 30 |
| 5 | 2b | 1 | dioxane | 88 | 94 | 6 |
| 6 | 2b | 1 | dioxane/$H_2O$ | 85 | 100 | 0 |
| 7 | 2c | 7 | dioxane | 92 | 50 | 50 |
| 8 | 2c | 1 | dioxane/$H_2O$ | 91 | 100 | 0 |
| 9 | 2d | 7 | dioxane | 92 | 50 | 50 |
| 10 | 2d | 1 | dioxane/$H_2O$ | 94 | 100 | 0 |
| 11 | 2e | 1 | dioxane/$H_2O$ | 93 | 100 | 0 |
| 12 | 2f | 7 | dioxane | 94 | 60 | 40 |
| 13 | 2f | 1 | dioxane/$H_2O$ | 92 | 100 | 0 |
| 14 | 2g | 7 | dioxane | 89 | 100 | 0 |
| 15 | 2g | 1 | dioxane/$H_2O$ | 95 | 100 | 0 |
| 16 | 2h | 1 | dioxane/$H_2O$ | 89 | 100 | 0 |
| 17 | 2i | 1 | dioxane/$H_2O$ | 90 | 100 | 0 |

[a]All reactions were performed using 1 mol % $PdCl_2$(rac-BINAP) and 300 mol % KF. The reactions were done at 100° C. for 2–24 h and progress of the reaction was monitored by TLC.
[b]Isolated yields were reported, and the ratio of homocoupling product vs crosscoupling product was determined by NMR.

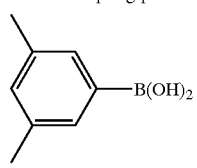

2a

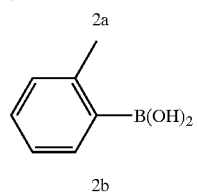

2b

TABLE 1-continued

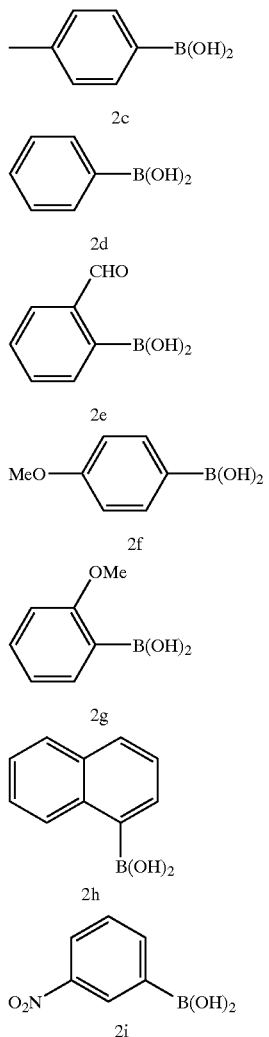

TABLE 1-continued

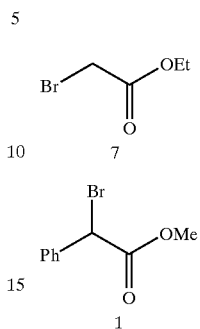

To explain the experimental results, possible reaction mechanisms are illustrated in Scheme 3. In the first step, the reaction is initiated by oxidative addition of an α-bromocarbonyl compound to a Pd(0) species to form compound 8. Intermediate 9 is formed after the first transmetallation and isomerization of 9 generates a palladium enolate intermediate 10, which undergoes a second transmetallation to yield the intermediate 12. Reductive elimination of 12 produces the homocoupling product 4. On the other hand, the reductive elimination of 9 gives the crosscoupling product 3. It is believed that isomerization of 9 to 10 and transmetallation of 10 with the aryl boronic acid 2 are reversible. The homocoupling path ($Sp^2$—$Sp^2$ coupling) is preferred when reductive elimination of 9 is inhibited using an α-substituted bromocarbonyl compound as a reagent (reductive elimination barrier of $Sp^2$–$Sp^3$ coupling is increased in the presence of a bulky $Sp^3$ group). In addition, presence of water will hydrolyse 11 and drive the reaction toward the intermediate 12. As the result, the homocoupling reaction is promoted.

Scheme 3

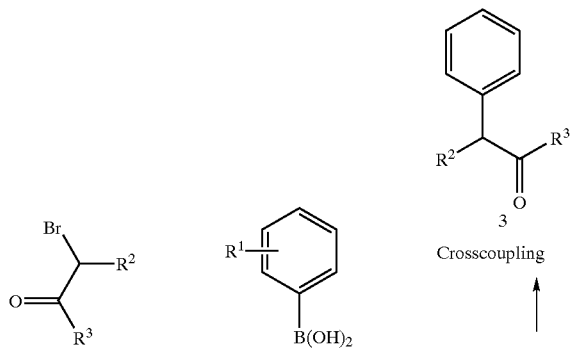

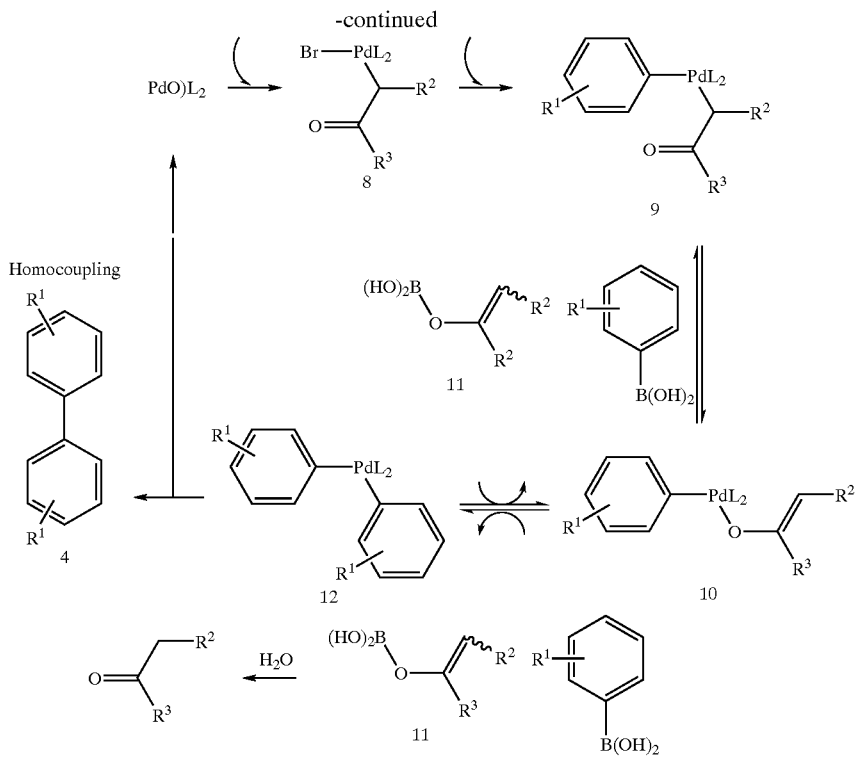

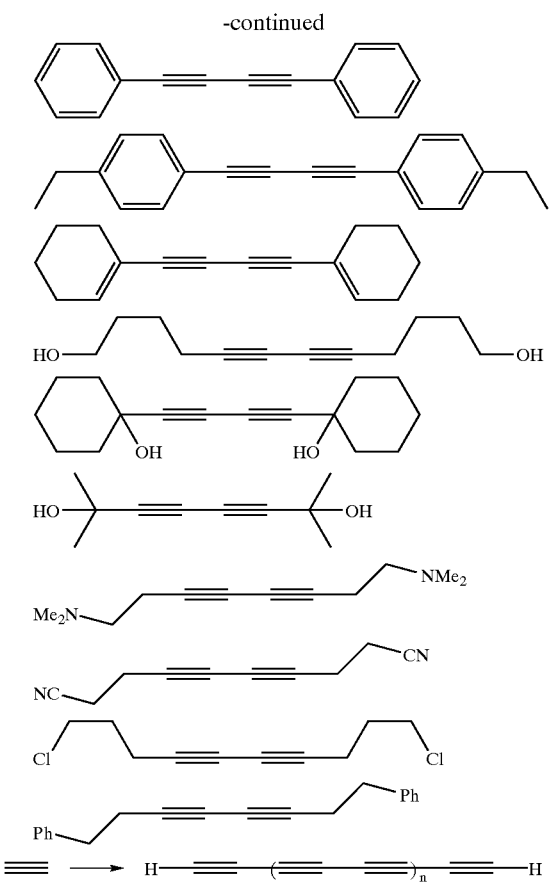

By employing a similar approach, homocoupling of many acetylenes under the mild conditions can be achieved. The transformation is illustrated below. The mild condition and high yield of this Sp—Sp coupling is suitable to from polymers and oligomers. The reaction can tolerate a variety of functional groups. An advantage is that the reaction can be carried out under an inert atmosphere, as opposed to an oxidative environment.

For example, it is expected that HC≡CH may polymerize to form Sp-carbon polymers, which can be converted as an useful material for its conducting properties. Since high molecular weight polymer has not be prepared, this materials may have unexpected properties. Using YC≡CH as the stopping agent, an oligomer such as YC≡C(C≡CC≡C)nC≡CY or YC≡C(C≡C)mC≡CY can be formed in the condensation polymerization. The Y capping group can be SiMe3, COOR, CN, aryl, substituted aryl, alkyl and substituted alkyl. Another possibility is to make HC≡CZC≡CH first, where Z is a bridge species. The bridge can be an aryl, substituted aryl, alkyl, substituted alkyl, heteroaryl species. Polymerization of this monomer will lead to interesting materials. Where this description is only outlined few chances of application of this new reaction, the potential application is broad for making materials for may applications. The art of modem acetyline chemistry will teach the practice of this chemistry in many key transformations [Diederich, F.; Stang, P. J. *Metal-catalyzed Cross-coupling Reaction,* Wiley-VCH, 1998].

Pd-Catalyzed Homocoupling Reaction

-continued

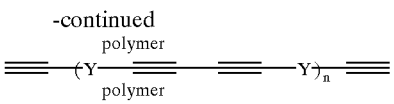

Y = a bridge species, include aryl, alkyl, substituted alkyl or substituted aryl
R = a terminal pecies, include aryl, alkyl, substituted alkyl or substituted aryl Among the more challenging problems of metal-catalyzed coupling is the Sp3—Sp3 coupling reactions (both intramolecular and intermolecular cases). Especially, the reaction has to tolerate beta H in both ends. By practicing an embodiment of the invention, coupling of a variety of alkynes has been achieved leading to the possibility of a variety of new polyalkynes. Especially, hydroboration of alkenes with 9-BBN or HB(OR)2 or asymmetric hydroboration of bis-alkenes will generate bis boron species. Coupling of these bis boron species can lead to formation up to four chiral centers. This strategy is very powerful for making many biologically active compounds. The hydroboration and coupling reaction is a significant method for forming a ring structure.

Pd-Catalyzed Homocoupling Reaction

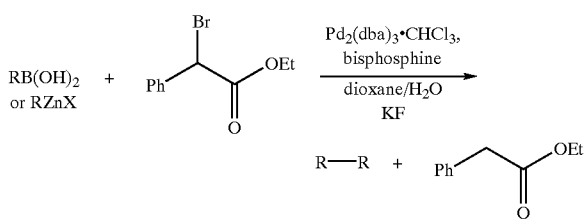

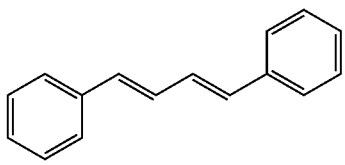

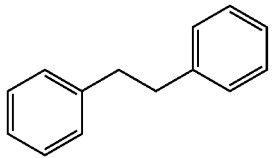

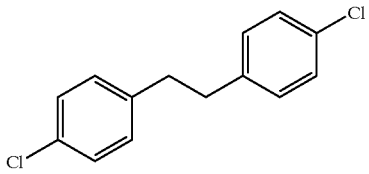

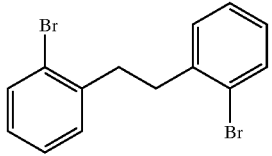

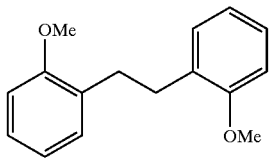

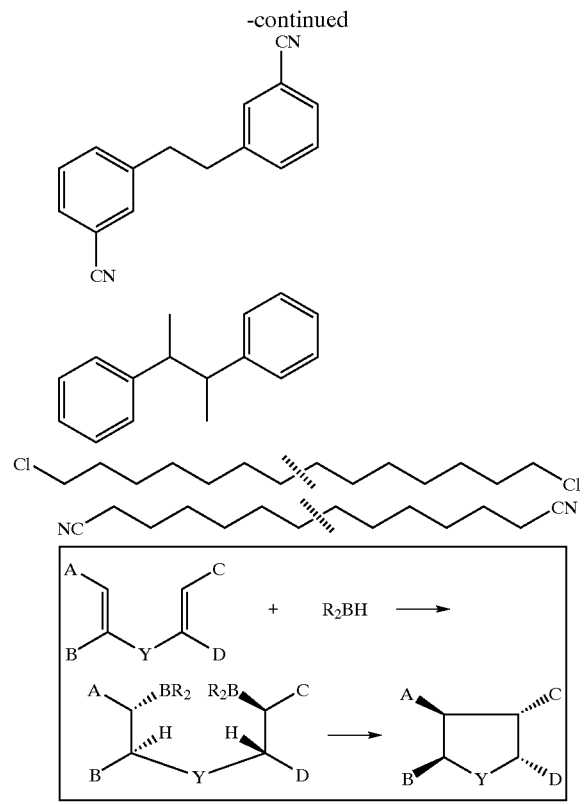

While the examples provided above relate to forming C—C bonds, it is conceivable that C-heteroatom bond forming reaction and some oxidation reaction can be performed using an alpha halo carbonyl compound as the oxidate. Because that metal-enolate and metal-halide has a different ability to do transmetallation and other transformation, we envision that several new reactions are possible.

Metal-Mediated Coupling Reactions

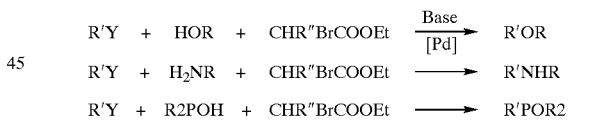

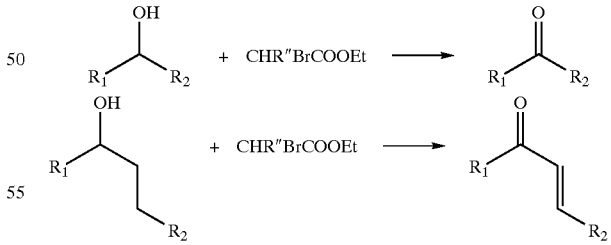

Y = B(OH)2, SnBu3, ZnCl, MgR2, SiMe3,, [Pd] = Pd(PPh3)4, PdCl2(PPh3 )2, PdCl2(dppf), Pd2(dba)3 + bisphosphine, Pd(OAc) + bisphosphine Base = NaHCO3, NaOR, Et3N, Et2NH, KF, Na2CO3, KOH $R_1$ and $R_2$ = H, alkyl, aryl, substituted alkyl, substituted aryl

EXPERIMENTAL

General Procedures: All reactions and manipulations were performed in a nitrogen-filled glovebox or using standard Schlenk techniques. Column chromatography was performed using EM silica gel 60 (230–400 mesh). $^1$H NMR were recorded on Bruker WP-200, DPX-300, and AMX-360 and DRX-400 spectrometers. Chemical shifts were reported in ppm down field from tetramethylsilane with the solvent resonance used as the internal standard.

Materials: Aryl boronic acids and α-bromocarbonyl compounds were purchased from Aldrich and were used directly without further purification. Dioxane was dried and distilled from sodium/benzophenone ketyl under nitrogen and was stored in a sure-sealed bottle.

A General Procedure for the Pd-catalyzed Homo-Coupling Reaction of Aryl Boronic Acids PdCl$_2$(rac-BINAP) (0.01 mmol), KF (3.0 mmol) and an aryl boronic acid (1 mmol) were added in a dried Schlenk tube. The mixture was purged with nitrogen, and solvents [dioxane (5 mL) or dioxane (4 mL) and H$_2$0 (1 mL)] were added. Under nitrogen, an α-bromo carbonyl compound [ethyl bromoacetate ester (0.6 mmol) or methyl α-bromophenylacetate ester (0.6 mmol)] was added and then the reaction mixture was stirred at 100° C. for 24 hours (h). After the reaction was completed, 5 mL of ethyl acetate and ca. 3–5 g of silica gel were added to the reaction mixture. The solvent was removed under vacuum and the solid mixture was loaded on a silica gel column to remove the Pd catalyst. The following compounds are known and references are provided:

sp$^2$—sp$^2$ data (Biaryl)

1,1'-Diphenic acid diethyl ester

Steliou, Kosta; Salama, Paul; Yu, Xiaoping; JACSAT; J. Amer.Chem.Soc.; EN; 114; 4; 1992; 1456–1462; Sheley; Patterson; ORMSBG; Org.Mass Spectrom.; 9; 1974; 731, 736; $^1$H NMR (360 MHz, CDCl$_3$) δ 7.99 (dd, J =1.4, 7.8, 2H), 7.50–7.48 (m, 2H), 7.41 (dt, J=1.3, 7.7, 2H), 7.18 (dd, J=1.0, 7.6, 2H), 4.01 (q, J=7.2, 4H), 0.96 (t, J=7.2, 6H).

1,1'-Diphenonitrile

Hassan, Jwanro; Penalva, Vincent; Lavenot, Laurence; Gozzi, Christel; Lemaire, Marc; TETRAB; Tetrahedron; EN; 54; 45; 1998; 13793–13804; $^1$H NMR (360 MHz, CDCl$_3$) δ 7.80 (d, J=7.5, 2H), 7.70 (dd, J=7.7, 7.5, 2H), 7.57-7.53 (m, 4H); $^{13}$C NMR (100 MHz, CDCl$_3$) δ 139.76, 131.74, 131.08, 128.75, 127.41, 115.77, 110.54.

2,2'-Dimethyl-biphenyl $^1$H NMR (360 MHz, CDCl$_3$) 7.35-7.26 (m, 6H), 7.14 (dJ,=7.8, 2H), 2.12 (s, 6H).

2,2'-Dimethoxy-biphenyl $^1$H NMR (360 MHz, CDCl$_3$) 7.34 (dddJ,=1.8, 7.9, 7.8, 2H), 7.27 (dd, J=1.8, 7.9, 2H), 7.05-6.97 (m, 4H), 3.78 (s, 6H).

4,4'-Dimethyl-biphenyl $^1$H NMR (300 MHz, CDCl$_3$) 7.62 (d,J=8.1, 4H), 7.37 (d,J=8.1, 4H), 2.53 (s, 6H).

4,4'-Dimethoxy-biphenyl $^1$H NMR (300 MHz, CDCl$_3$) 7.35 (d,J=8.5, 4H), 6.84 (d, J=8.5, 4H), 3.71 (s, 6H).

Biphenyl-2,2'-Dicarbaldehyde $^1$H NMR (360 MHz, CDCl$_3$) 9.79 (s, 2H), 8.01 (dd,J=1.1, 7.7, 2H), 7.60(ddd,J=1.1, 7.5, 7.6, 2H), 7.54(dd,J=7.7, 7.6, 2H),7.45(d,J=7.5, 2H).

3,3'-Dinitro-biphenyl $^1$H NMR (360 MHz, CDCl$_3$) 8.43 (tJ=2.0, 2H), 8.23 (d, J=8.0, 2H), 7.90 (d, J=8.0, 2H), 7.64 (t, J=8.0, 2H).

3, 5, 3', 5'-Tetramethyl-biphenyl $^1$H NMR (360 MHz, CDCl$_3$) 7.54 (s, 4H), 7.31 (s, 2H), 2.71 (s, 12H).

[1, 1']Binaphthalenyl $^1$H NMR (360 MHz, CDCl$_3$) 7.96-7.93 (m, 4H), 7.59 (t,J=8.1, 2H), 7.55-7.45 (m, 4H), 7.40(d, J=8.2, 2H), 7.28 (t, J=8.2, 2H).

Biphenyl $^1$H NMR (360 MHz, CDCl$_3$) 7.74 (d,J=7.8, 4H), 7.58 (dt, J=1.1, 7.5, 4H), 7.49(tt, J=1.1, 7.4, 2H).

Indan-1-One $^1$H NMR (400 MHz, CDCl$_3$) 7.72 (d,J=7.7, 1H), 7.55 (dd, J=7.7, 7.8, 1H), 7.45 (d, J=7.6, 1H), 7.36 (dd, J=7.6, 7.8, 1H), 3.13-3.09 (m, 2H), 2.67-2.64 (m, 2H).

Sp3—Sp3 coupling data

2,5-Dimethyl-2,5-diphenyl-hexanel,1'-(1,1,4,4-tetramethyl-1,4-butanediyl)bis-benzene Whitesides,G. M. et al.; JACSAT; J.Amer.Chem.Soc.; EN; 94; 1; 1972; 232–239; Richards,D. H.; Scilly,N. F.; JSOOAX; J.Chem.Soc.C; EN; 1969; 55–56.

2-Methyl-2-phenyl-propyl bromide

Tamao, Kohei; Yoshida, Jun-ichi; Akita, Munetaka; Sugihara, Yoshihiro; Iwahara, Takahisa; Kumada, Makoto; BCSJA8; Bull.Chem.Soc.Jpn.; EN; 55; 1; 1982; 255–260; $^1$H NMR (300 MHz, CDCl$_3$) δ 7.30-7.22 (m, 6H), 7.18-7.13 (m, 4H), 3.49 (s, 4H), 1.38 (s, 12H); $^{13}$C NMR (75MHz, CDCl$_3$) δ 146.38, 128.64, 128.45, 127.05, 126.35, 126.12, 47.33, 39.56, 29.42.

2,5-Dimethyl-2,5-diphenyl-hexane

Whitesides,G. M. et al.; JACSAT; J.Amer.Chem.Soc.; EN; 94; 1; 1972; 232–239; $^1$H NMR (300 MHz, CDCl$_3$) δ 7.31-7.28 (m, 4H), 7.21-7.19 (m, 6H), 1.38 (s, 4H), 1.23 (s, 12H); $^{13}$C NMR (75 MHz, CDCl$_3$) δ 149.71, 128.39, 126.32, 125.73, 39.28, 37.86, 29.52.

2-Methyl-2-phenyl-propan-1-ol

Balzer, Hartmut H.; Berger, Stefan; MRCHEG; Magn.Reson.Chem.; EN; 28; 5; 1990; 437–442; Ref. 1 5604628; Journal; Tamao, K.; Kakui, T.; Akita, M.; Iwahara, T.; Kanatani, R.; et al.; TETRAB; Tetrahedron; EN; 39; 6; 1983; 983–990; R. S. et al.; JACSAT; J.Amer.Chem.Soc.; EN; 92; 12; 1970; 3722–3729; $^1$H NMR (360 MHz, CDCl$_3$) δ 7.32-7.26 (m, 3H), 7.18-7.11 (m, 2H), 3.52 (s, 2H), 1.25 (s, 6H); $^{13}$C NMR (75 MHz, CDCl$_3$) δ 146.76, 129.14, 128.86, 128.62, 126.68, 126.63, 73.51, 40.51, 25.75

Phenylethanol

Journal; Aitken, R. Alan; Armstrong, Jill M.; Drysdale, Martin J.; Ross, Fiona C.; Ryan, Bruce M.; J.Chem.Soc.Perkin Trans.1; EN; 5; 1999; 593–604; Ref. 1 5570193; Journal; Flippin, Lee A.; Gallagher, David W.; Jalali-Araghi, Keyvan; JOCEAH; J.Org.Chem.; EN; 54; 6; 1989; 1430–1432; Ref. 1 5571848; Journal; Barluenga, Jose; Alonso-Cires, Luisa; Campos, Pedro J.; Asensio, Gregorio; SYNTBF; Synthesis; EN; 1; 1983; 53–55; $^1$H NMR (400 MHz, CDCl$_3$) δ 7.35-7.27 (m, 5H), 4.66 (s, 2H), 2.30 (br, 1H); $^{13}$C NMR (100 MHz, CDCl$_3$) δ 140.96, 128.98, 128.14, 127.50, 65.82; $^1$H NMR (400 MHz, CDCl$_3$) δ 7.30 (d, J=8.5, 2H), 7.26 (d, J=8.5, 2H), 4.63 (s, 2H), 1.89 (br, 1H); $^{13}$C NMR (100 MHz, CDCl$_3$) δ 139.65, 133.73, 129.07, 128.67, 64.91; Journal; Khotinsky; Melamed; CHBEAM; Chem.Ber.; 42; 1909; 3094; $^1$H NMR (400 MHz, CDCl$_3$) δ 7.27-7.08 (m, 7H), 2.83 (s, 2H)

2,2'-Dichloro-bibenzyl

Warren, Stuart; Wyatt, Paul; JCPRB4; J.Chem.Soc.Perkin Trans.1; EN; 2; 1998; 249–256; Tashiro,M. et al.; JOCEAH; J.Org.Chem.; EN; 43; 1978; 1413–1419; $^1$H NMR (360 MHz, CDCl$_3$) δ 7.38-7.32 (m, 2H), 7.18-7.11 (m, 6H), 2.95 (s, 4H); $^{13}$C NMR (360 MHz, CDCl$_3$) δ 139.37, 134.43, 131.02, 129.89, 127.96, 127.17, 34.21.

1,2-Bis-(2-bromo-phenyl)-ethane

Kelly, T. Ross; Li, Qun; Bhushan, Vidya; TELEAY; Tetrahedron Lett.; EN; 31; 2; 1990; 161–164; Yamato, Takehiko; Sakaue, Naozumi; Komine, Masayasu; Nagano, Yoshiaki; JRMPDM; J.Chem.Res.Miniprint; EN; 7; 1997; 1708–1735; $^1$H NMR (360 MHz, CDCl$_3$) δ 7.71 (d, J=8.0Hz, 2H), 7.40-7.34 (m, 4H), 7.25–7.71 (m, 2H), 3.21 (s, 4H); $^{13}$C NMR (360 MHz, CDCl$_3$) δ 141.01, 133.30, 131.05, 127.87, 124.92, 36.87.

1-Bromo-6-choro-hexane $^1$H NMR (400 MHz, CDCl$_3$) δ 3.52 (t, J=6.6 Hz, 2H), 3.40 (t, J=6.7 Hz, 2H), 1.87-1.80(m, 2H), 1.79-1.75(m, 2H), 1.47-1.41(m, 4H); $^{13}$C NMR (75 MHz, CDCl$_3$) δ 45.30, 34.08, 32.94, 32.75, 27.82, 26.43.

1,12-Dicholo-dodecane

Turro, Nicholas J.; Han, Nianhe; Lei, Xue-gong; Fehlner, James R.; Abrams, Lloyd; JACSAT; J.Amer.Chem.Soc.; EN; 117; 17; 1995; 4881–4893; $^1$H NMR (300 MHz, CDCl$_3$) δ 3.51 (t, J=6.8 Hz, 4H), 7.271.79-1.70 (m, 4H), 1.42-1.38 (m, 4H), 1.26-1.23 (m, 12H); $^{13}$C NMR (90MHz, CDCl$_3$) δ 45.56, 33.04, 29.86, 29.26, 27.26.

Hexadecane

Chatgilialoglu, C.; Guerrini, A.; Lucarini, M.; JOCEAH; J.Org.Chem.; EN; 57; 12; 1992; 3405–3409; $^1$H NMR (400 MHz, CDCl$_3$) δ 1.30-1.19 (m, 26H), 0.86 (t, J=6.8Hz, 6H); $^{13}$C NMR (100 MHz, CDCl$_3$) δ 32.33, 30.10, 30.06, 29.77, 23.10.

Tetradecanedinitrile

Saotome,K. et al.; BCSJA8; Bull.Chem.Soc.Jpn.; EN; 39; 1966; 480–484;

6-bromo-hexanoic acid ethyl ester

McHintosh, John M.; Pillon, Lilianna Z.; Acquaah, Samuel O.; Green, James R.; White, Graham S.; CJCHAG; Can.J.Chem.; EN; 61; 1983; 2016–2021; Somekawa, Kenichi; Okuhira, Hiroyuki; Sendayama, Masayuki; Suishu, Takaaki; Shimo, Tetsuro; JOCEAH; J.Org.Chem.; EN; 57; 21; 1992; 5708–5712; $^1$H NMR (300 MHz, CDCl$_3$) δ 4.03 (q, J=7.2, 2H), 3.23 (t, J=6.8, 2H), 2.18 (t, J=7.3, 2H), 1.76-1.71 (m, 2H), 1.55-1.48 (m, 2H), 1.36-1.31(m, 2H), 1.13 (t, J =7.2, 3H); $^{13}$C NMR (75 MHz, CDCl$_3$) δ 173.81, 60.67, 34.47, 33.96, 32.80, 28.03, 24.50, 14.69.

Dodecanedioic acid diethyl ester

Menger, F. M.; Wood, M. G.; Richardson, S.; Zhou, Q.; Elrington, A. R.; Sherrod, M. J.; JACSAT; J.Amer.Chem.Soc.; EN; 110; 20; 1988; 6797–6803; $^1$H NMR (400 MHz, CDCl$_3$) δ 4.04 (q, J=7.2, 4H), 2.21(t, J=7.4, 4H), 1.58-1.50 (m, 4H), 1.24-1.16 (m, 18H)

1,2-Diphenyl-ethane

Hartman, Stephen J.; Kelusky, Eric C.; CJCHAG; Can.J.Chem.; EN; 60; 1982; 2654–2660; Marquet, Jorge; Moreno-Manas, Marcial; Pacheco, Pedro; Prat, Maria; Katritzky, Alan R.; Brycki, Bogumil; TETRAB; Tetrahedron; EN; 46; 15; 1990; 5333–5346; $^1$H NMR (400 MHz, CDCl$_3$) δ7.30-7.26 (m, 4H), 7.21-7.18 (m, 6H), 2.92 (s, 4H); $^{13}$C NMR (100 MHz, CDCl$_3$) δ 142.19, 128.86, 128.75, 126.33, 38.37.

2,3-Diphenyl-butane

Kim, Seung-Hoi; Rieke, Reuben D.; JOCEAH; J.Org.Chem.; EN; 65; 8; 2000; 2322–2330; $^1$H NMR (400 MHz, CDCl$_3$) δ 7.25-7.21 (m, 2H), 7.15-7.13 (m, 3H), 7.10-7.06 (m, 2H), 7.02-7.00(m, 1H), 6.94-6.92(m, 2H), 2.88–2.84 (m, 1.2H), 2.73-2.71 (m, 0.8H), 1.20 (dd, J=1.8, 5.0, 3.6H), 0.95 (dd, J=2.0, 4.8, 2.4H); $^{13}$C NMR (100 MHz, CDCl$_3$) δ 146.91, 146.26, 128.71, 128.25, 128.20, 128.04, 126.48, 126.12, 47.69, 46.90, 21.47, 18.37.

1,2-diphenyl-ethanone

Journal; Kawatsura, Motoi; Hartwig, John F.; JACSAT; J. Amer. Chem. Soc.; EN; 121; 7; 1999; 1473–1478; $^1$H NMR (360 MHz, CDCl$_3$) δ 7.93 (d, J=7.7, 2H), 7.48 (td, J=1.2, 7.3, 1H), 7.37 (dd, J=7.3, 7.7, 2H), 7.26-7.23 (m, 2H), 7.20-7.15(m, 3H), 4.20 (s, 2H); $^{13}$C NMR (100 MHz, CDCl$_3$) δ 198.04, 137.00, 134.95, 133.59, 129.89, 129.09, 129.06, 129.03, 127.31, 45.91.

sp$^2$—sp$^2$ data (vinyl—vinyl) data 1,4-Diphenyl-buta-1,3-diene

Nishihara, Yasushi; Ikegashira, Kazutaka; Toriyama, Fumihiko; Mori, Atsunori; Hiyama, Tamejiro; BCSJA8; Bull.Chem.Soc.Jpn.; EN; 73; 4; 2000; 985–990; $^1$H NMR (400 MHz, CDCl$_3$) δ 7.48 (d, J=7.5 Hz, 4 H), 7.38 (dd, J=7.5, 7.0, 4H), 7.28 (t, J=7.0, 1H), 6.95 (dd, J=14.7, 2.7 Hz, 2 H), 6.71 (dd, J=14.7Hz, 2.7H); $^{13}$C NMR (90 MHz, CDCl$_3$) δ 135.35, 130.83, 127.25, 126.67, 125.57, 124.40.

sp—sp Coupling data

Diphenylbutadiyne

Aitken, R. Alan; Herion, Hugues; Horsburgh, Caroline E. R.; Karodia, Nazira; Seth, Shirley; JCPRB4; J.Chem.Soc.Perkin Trans.1; EN; 5; 1996; 485–490; $^1$H NMR (400 MHz, CDCl$_3$) δ7.55-7.50 (m, 4H), 7.37-7.32 (m, 6H)

2,7-Dimethyl-octa-3,5-diyne-2,7-diol

Raj, C. Paul; Braverman, S.; SYNCAV; Synth.Commun.; EN; 29; 15; 1999; 2629–2638; $^1$H NMR (400 MHz, CD$_2$Cl$_2$) δ 2.02 (s, 2H), 1.42 (s, 12H); $^{13}$C NMR (100 MHz, CD$_2$Cl$_2$)

δ 84.92, 66.65, 66.17, 31.64; $^1$H NMR (400 MHz, CDCl$_3$)δ 7.55-7.50 (m, 4H), 7.37-7.32 (m, 6H).

Bis-(4-ethyl-phenyl)-butadiyne

Uchida,A. et al.; JOCEAH; J.Org.Chem.; EN; 37; 23; 1972; 3749–3750; $^1$H NMR (360 MHz, CDCl$_3$)δ 7.43 (d, J=8.1, 4H), 7.15 (d, J=8.1, 4H), 2.67(q, J 7.6, 4H), 1.25(t, J=7.6, 6H); $^{13}$C NMR (90 MHz, CDCl$_3$) δ 146.1, 132.9, 128.4, 119.5, 82.0, 73.9, 29.3, 15.6.

4,4'-Di-n-propyldiphenyldiacetylene $^1$H NMR (360 MHz, CDCl$_3$) δ 7.36 (d, J=8.2, 4H), 7.02(d, J=8.2, 4H), 2.52(t, J=7.6, 4H), 1.78-1.54(m, 4H), 0.91(t, J=7.3, 6H); $^{13}$C NMR (90 MHz, CDCl$_3$) δ 142.0, 132.7, 131.6, 130.6, 119.7, 62.7, 37.8, 24.8, 14.4.

Di-cyclohexy-1-enyl-butadiyne $^1$H NMR (300 MHz, CDCl$_3$) δ 6.23-6.21(m, 2H), 2.10-2.09 (m, 8H), 1.61-1.55(m, 8H); $^{13}$C NMR (75 MHz, CDCl$_3$) δ 138.5, 120.3, 83.0, 71.9, 29.1, 26.3, 22.5, 21.7.

Hexadeca-7,9-diyne $^1$H NMR (360 MHz, CDCl$_3$) δ 2.22 (t, J=6.8 MHz, 4H), 1.53-1.47 (m, 4H), 1.40-1.20 (m, 12H), 0.87 (t, J=6.6, 6H); $^{13}$C NMR (90 MHz, CDCl$_3$) δ 77.9, 65.7, 31.7, 28.9, 28.7, 22.9, 19.6, 14.4.

Dodeca-5,7-diyne-1,12-diol $^1$H NMR (360MHz, CDCl$_3$) δ 3.65(t, J=6.2, 4H), 2.28(t, J=6.5, 4H), 1.70-1.57 (m, 8H), 1.34 (br, 2H); $^{13}$C NMR (90MHz, CDCl$_3$) δ 77.6, 66.0, 62.7, 32.1, 25.0, 19.4.

1,4-Bis(1-hydroxycyclohexyl) buta-1,3-diyne

TETRAB; Tetrahedron; EN; 34; 1978; 1323–1332; $^1$H NMR (CDCl$_3$) δ 1.98 (br, 2H), 1.92-1.88 (m, 4H), 1.74-1.66 (m, 4H), 1.61-1.48 (m, 8H), 1.28-1.21 (m, 4H); $^{13}$C NMR (CDCl$_3$) δ 83.4, 69.6, 68.7, 40.1, 25.4, 23.5.

1,1'-butadiynediyl-bis-cyclopentanol $^1$H NMR (360 MHz, CDCl$_3$) δ 2.02-1.92 (m, 8H), 1.87-1.67 (m, 8H), 1.20 (br, 2H), $^{13}$C NMR (90 MHz, CDCl$_3$) δ 82.2, 73.7, 66.3, 41.3, 22.3.

1,8-diphenyl-octa-3,5-diyne $^1$H NMR (360 MHz, CDCl$_3$) δ 7.25-7.11 (m, 10H), 2.76 (t, J=7.4, 4H), 2.46 (t, J=7.5, 4H); $^{13}$C NMR (90 MHz, CDCl$_3$) δ 140.6, 128.9, 128.8, 126.8, 77.3, 66.3, 35.3, 21.9.

2,7-Dimethyl-octa-3,5-diyne-2,7-diol

Raj, C. Paul; Braverman, S.; SYNCAV; Synth.Commun.; EN; 29; 15; 1999; 2629–2638; $^1$H NMR (400 MHz, CD$_2$Cl$_2$) δ 2.02 (s, 2H), 1.42 (s, 12H); $^{13}$C NMR (100 MHz, CD$_2$Cl$_2$) δ 84.92, 66.65, 66.17, 31.64.

Tetracosa-11,13-diyne $^1$H NMR (360 MHz, CDCl$_3$) δ 2.22 (t, J=6.6, 4H), 1.54-1.45 (m, 4H), 1.37-1.24 (m, 28H), 0.86 (t, J=6.7, 6H); $^{13}$C NMR (90MHz, CDCl$_3$) δ 77.2, 64.9, 31.5, 29.2, 29.1, 28.9, 28.7, 28.5, 28.0, 22.3, 18.8, 13.7.

Deca-4,6-diynedinitrile $^1$H NMR (360 MHz, CDCl$_3$) δ 2.64(t, J=6.4, 4H), 2.57(t, J=6.4, 4H); $^{13}$C NMR (90 MHz, CDCl$_3$) δ 118.0, 74.3, 67.8, 17.5, 17.0.

Dichloro-deca-4,6-diyne $^1$H NMR (CDCl$_3$) δ 3.64 (t, J=6.2, 4H), 2.46 (t, J=6.8, 4H), 2.05-1.94 (m, 4H); $^{13}$C NMR (CDCl$_3$) δ 76.2, 66.5, 43.8, 31.5, 17.7.

Polymerization of alkynes

A wide variety of alkynes can be made by combining a alkyne with a catalysts and an alpha-halo carbonyl. These alkynes can be polymerized alone or with an end-capping agent. In an embodiment of the present invention, one or more bonds is formed between one of more alkynes to form an oligomer or polymer. For example, the polymer can have the following structure:

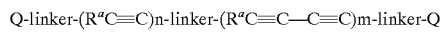

or

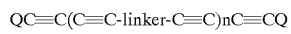

wherein: R$^a$ is a substituted or unsubstituted diradical of an alkane, alkene, alkyne, if present; Q is H, a metal, an organometallic species, or a substituted or unsubstituted silane, SiMe$_3$, COOR', aryl, alkyl, siloxane, CN, or, CONHR'; where R' is an alkyl or aryl group; linker is a joining bond, i.e. the linker denotes a bond between the two groups. Linker also represents a substituted or unsubstituted diradical of an alkane, alkene, alkyne, aryl, arylene, aromatic, or siloxane. These polymers can be of a high molecular weight, e.g. where n or m has a value as high millions. In one aspect, the values of n or m is from 1 to 100,000, e.g., n or m is from 1 to 1,000. In another aspect polymeric materials of where n and/or m is 10 to 100 can be formed. An example of a polyacetylene end-capped with phenylacetylene is provided below.

A mixture of Acetylene (194 mg, 1 mmol), CuI (9.5 mg, 0.05 mmol), PdCl$_2$(BINAP) (40 mg, 0.05 mmol), Desyl chloride (138.4 mg, 0.6 mmol) and DABCO (134.4 mg, 1.2 mmol) in 5 ml THF was stirred at room temperature. To this solution, a small amount of Phenyl acetylene (10.4 mg, 0.1 mmol) was added and the reaction mixture was stirred for 2 days. The solvent was removed in vacuo and 10 ml. of MeOH was added to the residue. The solid was filtered and washed a few times with methanol. After drying, a brownish black solid was obtained.

The following table illustrates the polymerization of a wide variety of alkynes by the above approach. It is understood that the polymeric products are produced from the corresponding alkyne. For example, the polymer of entry 1 is produced from the 1,7-dioctyne. The repeating unit is indicated by the subscript "n".

| Polymer | Yield | Characterization[1] |
|---|---|---|
| 1  −(≡−CH₂CH₂CH₂CH₂−≡)ₙ− | 51% | GPC - 994<br>color - Brownish yellow solid |
| 2  −(≡−CH₂CH₂CH₂CH₂CH₂−≡)ₙ− | 55% | solid state NMR - 137, 129, 78.8, 68.7, 28.9, 19.7;<br>GPC - 1194<br>color - Same as above |
| 3  (2,5-dibutoxyphenylene with two −(≡)ₙ− arms) | 45% | U.V.-Vis - 420(max), 316, 332<br>NRM - 0.6, 0.83, 0.97, 1.23, 1.35, 1.52, 1.79, 2.15, 3.96, 6.95<br>GPC - 4575<br>Color - Orange/red |
| 4  Ph−≡−(≡)ₙ−≡−Ph | — | U.V.-Vis - 204(Max), 638, 650<br>I.R. - 3054, 2150, 1597, 696<br>$^{13}$C NMR solid - 112<br>GPC - 2321<br>color - Black<br>color - Black |
| 5  Me₃Si−≡−(≡)ₙ−≡−SiMe₃ | — | |
| R−≡−(≡)ₙ−≡−R | | U.V.-Vis - 244<br>color - Brown |
| 6  R = CH₃C(O)OCH₂CH₂OCH₂CH₂CH₂CH₂Si(−O−Si−C₄H₉) | | |

[1]GPC (Gel Permeation Chromatography) relates to an approximate molecular weight of the product.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein.

What is claimed is:

1. A method of forming a chemical bond, the method comprising:
   combining at least one α-halo carbonyl compound with at least one transmetallation reagent comprising a target compound; and
   forming a chemical bond by substantially homocoupling the target compound.

2. The method of claim 1, comprising forming the chemical bond in the presence of a catalyst selected from the group consisting of Pd(0), Ni(0), Rh(I), Pt(0), Ir(0), Cu(I), Mo(0), Mo(II), and Ru(II).

3. The method according to claim 2, wherein the transmetallation reagent comprises a boron derivative of ROH, RNH₂, RN(R')H, RSH, or R2P(O)H, wherein R and R' are independently a substituted aryl or arkyl group.

4. The method of claim 1, wherein the transmetallation reagent contains one or more elements selected from the group consisting of B, Sn, Al, Zn, Mg, Zr, Cu, Hg, and Si.

5. The method of claim 1, wherein the α-halo carbonyl compound is a α-bromo carbonyl compound.

6. The method according to claim 1, comprising an alkyl or aryl boronic acid as the target compound undergoing chemical bond formation.

7. The method according to claim 1, comprising an alkyl or aryl Zn compound as the target compound and coupling the alkyl or aryl Zn compound as the bond forming step.

8. The method of claim 1, wherein the catalyst is selected from the group consisting of PtCl₂; H₂PtCl₄; Pd₂(DBA)₃; Pd(OAc)₂; PdCl₂(RCN)₂; PdCl₂(diphosphine); (Pd (allyl)Cl)₂; Pd(PR₃)₄; (Rh(NBD)₂)X; (Rh (NBD)Cl)₂; (Rh (COD)Cl)₂; (Rh(COD)₂)X; Rh(acac)(CO)₂; Rh(ethylene)₂ (acac); (Rh(ethylene)₂Cl)₂; RhCl(PPh₃)₃; Rh(CO)₂Cl₂; Ru(arene)X₂(diphosphine); Ru(aryl group)X₂; Ru(RCOO)₂ (diphosphine); Ru(methallyl)2(diphosphine); Ru(aryl group)X₂(PPh₃)₃; Ru(COD)(COT); Ru(COD)(COT)X; RuX₂(cymen); Ru(COD)ₙ; Ru(aryl group)X₂(diphosphine); RuCl₂(COD); (Ru(COD)₂)X; RuX₂(diphosphine); RuCl₂(=CHR)(PR'₃)₂; Ru(ArH)Cl₂; Ru(COD)(methallyl)₂; (Ir (NBD)₂Cl)₂; (Ir(NBD)₂)X; (Ir(COD)₂Cl)₂; (Ir(COD)₂)X; CuX (NCCH₃)₄; Cu(OTf); Cu(OTf)₂; Cu(Ar)X; CuX; Ni(acac)₂; NiX₂; (Ni(allyl)X)₂; Ni(COD)₂; NiCl₂ (diphosphine); and MoO₂(acac)₂; wherein each R and R' is independently selected from the group consisting of: alkyl or aryl; Ar is an aryl group; and X is I, Br, Cl, OTf, BF₄, SbF₆, BAr₄.

9. The method of claim 8, wherein the diphosphine is dppe, dppp, dppb, dppf, rac-Binap, DuPhos, BINAP, BPPM, DIPAMP, DIOP, MCCPM, BCPM, BICP, PennPhos, BPE, ChiraPhos, NorPhos, Degphos, BPPFA, JosiPhos, TRAP, TolBINAP, H8-BINAP, BINAPO, MOP, BINAPHOS, BIPHEMP, SEGPHOS, TUNAPHOS, KetalPhos, f-KetalPhos, HydroPhos, f-HydroPhos, Binaphane, f-Binaphane, FAP.

10. The method of claim 1, further comprising admixing a base selected from the group consisting of Et$_3$N, DABCO, Et$_2$NH, NaOR, Na$_2$CO$_3$, KF, K$_3$PO$_4$, NaOAc, KOH, and R$^b_2$NX, where R$^b$ is one or more alkyl groups and X is an anion.

11. The method of claim 1, comprising forming one or more bonds between one of more alkynes to form an oligomer or polymer having the following structure:

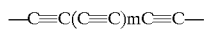

or

wherein:
the linker is a substituted or unsubstituted diradical of an alkane, alkene, alkyne, aryl, arylene, aromatic group, or siloxane;
n is 1 to 100000; and
m is 1 to 100000.

12. The method of claim 11, wherein the oligomer or polymer has the following structure:

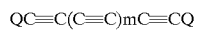

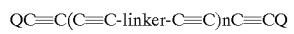

wherein:
Q is H, a metal, a substituted or unsubstituded silane, SiMe$_3$, COOR',aryl, alkyl, siloxane, CN, or CONHR'; where R' is an alkyl or aryl group.

13. The method of claim 1, wherein the homocoupling occurs in at least 70% yield.

14. The method of claim 13, wherein the α-halo carbonyl compound if an α-bromophenyl carbonyl compound.

15. A method of coupling a boron containing compound, the process comprising:
combining at least one α-halo carbonyl compound with at least one catalyst and a boron compound; and
substantially coupling boron containing compound with itself.

16. The method of claim 15, comprising forming one or more bonds between one as more alkynes containing boron as the boron containing compound.

17. The method of claim 16, wherein the alkyne is acetylene.

18. The method of claim 16, comprising polymerizing acetylene or diacetylene.

19. The method of claim 15, wherein the α-halo carbonyl compound is an α-bromophenyl carbonyl compound.

* * * * *